United States Patent [19]

Ayres et al.

[11] Patent Number: 4,707,170

[45] Date of Patent: Nov. 17, 1987

[54] STAGED MULTICOMPONENT REFRIGERANT CYCLE FOR A PROCESS FOR RECOVERY OF $C_{3+}$ HYDROCARBONS

[75] Inventors: Calvin L. Ayres, Allentown; Howard C. Rowles, Center Valley, both of Pa.

[73] Assignee: Air Products and Chemicals, Inc., Allentown, Pa.

[21] Appl. No.: 889,061

[22] Filed: Jul. 23, 1986

[51] Int. Cl.$^4$ ............................................. F25J 3/02
[52] U.S. Cl. ............................................. 62/24; 62/40
[58] Field of Search ............................... 62/23, 24, 40

[56]  References Cited

U.S. PATENT DOCUMENTS

| | | | |
|---|---|---|---|
| 3,702,063 | 11/1972 | Etzbach et al. | 62/23 |
| 3,929,438 | 12/1975 | Harper et al. | 62/9 |
| 4,002,042 | 1/1977 | Pryor et al. | 62/28 |
| 4,152,129 | 5/1979 | Trentham et al. | 62/40 |
| 4,229,195 | 10/1980 | Forg | 62/40 |
| 4,270,940 | 6/1981 | Rowles et al. | 62/28 |
| 4,272,269 | 6/1981 | Hammond et al. | 62/17 |
| 4,272,270 | 6/1981 | Higgins | 62/24 |
| 4,303,427 | 12/1981 | Krieger | 62/9 |
| 4,356,014 | 10/1982 | Higgins | 62/28 |
| 4,381,418 | 4/1983 | Gewartowski et al. | 62/23 |
| 4,401,450 | 8/1983 | Schramm | 62/13 |
| 4,443,238 | 4/1984 | Beddome et al. | 62/17 |
| 4,456,460 | 6/1984 | Apffel | 62/26 |
| 4,461,634 | 7/1984 | Duckett et al. | 62/11 |
| 4,482,369 | 11/1984 | Carson et al. | 62/18 |
| 4,507,133 | 3/1985 | Khan et al. | 62/29 |
| 4,519,825 | 5/1985 | Bernhard et al. | 62/28 |
| 4,526,596 | 7/1985 | Baggio et al. | 62/40 |
| 4,548,629 | 10/1985 | Chiu | 62/40 |
| 4,584,006 | 4/1986 | Apffel | 62/30 |

FOREIGN PATENT DOCUMENTS 2146751A 4/1985 United Kingdom .

OTHER PUBLICATIONS

Oil and Gas Journal Article by D. H Mackenzie and S. T. Donnelly "Mixed Refrigerants Proven Efficient in Natural-gas-Liquids $C_{3+}$ Recovery Process" Mar. 4, 1985, pp. 116–120.

Oil and Gas Journal Article by T. R. Tomlinson and R. Banks "LPG Extraction Process Cuts Energy Need", Jul. 15, 1985, pp. 82–88.

Primary Examiner—Ronald C. Capossela
Attorney, Agent, or Firm—G. L. Chase; W. F. Marsh; J. C. Simmons

[57] ABSTRACT

The present invention is a process for phase separating, dephlegmating and optionally distilling a feed gas stream to recover a light gas product and a heavy hydrocarbon product wherein a predominant amount of the refrigeration for the process is provided by a two temperature and two pressure stage multicomponent closed-circuit refrigeration cycle.

15 Claims, 2 Drawing Figures

STAGED MULTICOMPONENT REFRIGERANT CYCLE FOR A PROCESS FOR RECOVERY OF $C_{3+}$ HYDROCARBONS

TECHNICAL FIELD

The present invention is directed to the resolution of light hydrocarbon containing streams using low temperature phase separation and dephlegmation. wherein the refrigeration for such separation and dephlegmation is predominantly provided by a two-stage, multicomponent, closed-circuit refrigeration cycle. More specifically, the present invention is directed to the recovery of $C_{3+}$ hydrocarbons from a light gas and light hydrocarbon containing stream using the sequential steps of cooling, phase separation, dephlegmation and optional distillation wherein the refrigeration necessary for such processing is derived predominantly from a two temperature and two pressure stage, multicomponent, closed-circuit refrigeration cycle.

BACKGRDUND OF THE PRIOR ART

It is known in the prior art to resolve various light gas streams containing hydrocarbons into a purified light gas stream as one product of the resolution and a heavier hydrocarbon stream, such as a $C_{3+}$ hydrocarbon stream, as another product of the resolution. It is also known in the prior art to perfect this resolution with various combinations of low temperature, separatory process steps, including phase separation, distillation and the use of refluxing heat exchangers, sometimes referred to as dephlegmators. It is specifically known to use a combination of low temperature cooling of a feed gas stream followed by phase separation and subsequent dephlegmation to resolve a light gas stream and a heavy hydrocarbon stream from a feed gas. The heavy hydrocarbon stream can be further resolved in a separatory column.

For example, in UK Patent Application No. GB2146751A, published April 24, 1985 to Tomlinson and Cummings, the recovery of LPG or NGL and sales gas from a gaseous hydrocarbon feed is conducted by cooling the feed against process streams and/or refrigeration before phase separating into light gas and heavy liquid streams followed by dephlegmation of the light gas stream and column stripping of the heavy liquid stream with recycle of the overhead vapor from the column back to feed. The UK patent application at page 4, line 37 recites that, "The two-stage cascade refrigerator employed in the process described in FIG. 2 may be replaced by some other form of external refrigeration, if desired. For example, a single loop vapor compression refrigerator employing a mixed refrigerant may be employed, but the power saving will not be so great."

In the article, "Mixed Refrigerants Proven Efficient in Natural Gas Liquids Recovery Process", by D. H. MacKenzie and S. T. Donnelly, appearing in the Oil and Gas Journal, Mar. 4, 1985, in FIG. 2 at page 117, a mixed refrigerant gas separation cycle is disclosed in which a single pressure, phase separated, closed-circuit refrigerant cycle is utilized with a multicomponent refrigerant. The separation process disclosed in FIG. 2 of that article does not specifically call for a reflux in the heat exchanger or for dephlegmation.

In another article titled, "LPG Extraction Process Cuts Energy Needs" by T. R. Tomlinson and R. Banks, appearing in the Oil and Gas Journal, July 15, 1985 at page 82, the Petroflux process identified in FIG. 2 which is similar to the UK patent application identified above is disclosed and the refrigeration system labeled in FIG. 2 is described in the text in the following manner:

"In many cases, a cascade refrigeration cycle (propane and ethane or ethylene) is preferred.", . . . "In special circumstances, a mixed refrigerant cycle may be considered for the process." . . . and "A single loop vapor compression refrigeration cycle employing mixed refrigerant has already been mentioned as a possible alternative." Accordingly, the disclosure of this article is limited to a single loop vapor compression refrigeration cycle, or a cascade refrigeration cycle.

U.S. Pat. No. 3,929,438 discloses a natural gas processing cycle wherein NGL components are removed from natural gas in a heat exchanger and phase separator wherein the heat exchanger is cooled by refrigeration from a multistaged closed-circuit refrigerant cycle wherein the refrigerant may preferably be a multicomponent refrigerant as specified in col. 1, lines 42–47. The cooling from the refrigeration cycle is performed in a single heat exchanger against the entire natural gas feed stream.

In U.S. Pat. No. 4,456,460, natural gas is separated from ethane, propane and heavier hydrocarbons in a cycle utilizing heat exchange, phase separation and a distillation column, wherein the refrigeration is supplied by a single stage, multicomponent, closed-circuit refrigeration cycle.

U.S. Pat. No. 4,584,006 discloses a process for recovery of $C_{3+}$ compounds from natural gas using a multicomponent refrigerant in several circuits.

Other prior art of general relevance showing various individual steps that are relevant to the technical field of the present invention, including phase separation, natural gas processing, distillation and dephlegmation include: U.S. Pat. Nos. 4,002,042; 4,270,940; 4,272,269; 4,272,270; 4,303,427; 4,356,014; 4,381,418; 4,401,450; 4,443,238; 4,461,634; 4,482,369; 4,507,133; 4,519,825; 4,526,596.

BRIEF SUMMARY OF THE INVENTION

The present invention is a process for the low temperature separation of a feed gas into a heavy hydrocarbon product containing $C_{3+}$ hydrocarbons and a light gas stream containing $H_2$, $N_2$, CO, $CO_2$, methane and/or $C_2$ hydrocarbons or other light gases using a two temperature and two pressure stage closed-circuit multicomponent refrigerant cycle comprising the steps of cooling the feed gas to effect the partial condensation of said gas by indirect heat exchange against a relatively high temperature and pressure stage of said multicomponent refrigerant, initially phase separating the partially condensed feed gas into a heavy liquid containing heavy hydrocarbons and a vapor stream containing light feed gas components, rectifying the vapor stream by low temperature dephlegmation to produce a light gas stream and additional heavy liquid wherein the rectification is obtained at least in part by indirect heat exchange against a relatively low temperature and pressure stage of said multicomponent refrigerant, removing said heavy liquid as a heavy hydrocarbon product containing $C_{3+}$ hydrocarbons, removing the light gas stream as a product light gas stream containing $H_2$, $N_2$, CO, $CO_2$, methane and/or $C_2$ hydrocarbons or other light gases and providing the predominant amount of the refrigeration for the process from said multicomponent refrigerant cycle wherein the refrigerant is partially condensed, phase separated, the vapor phase is cooled, condensed and expanded to a relatively low temperature and pressure and rewarmed against the vapor stream being rectified and then recompressed to an intermediate pressure, while the liquid phase is cooled and expanded to a relatively higher temperature and pressure, rewarmed against feed gas, mixed with the intermediate pressure refrigerant and the combined refrigerant is compressed to an elevated pressure and aftercooled sufficiently to partially condense the refrigerant to complete the cycle.

Preferably, the process is operated so as to recover 90% or more of the $C_3$ hydrocarbons of the feed gas stream in said heavy hydrocarbon product.

Optimally, the process of the present invention is operated to recover 98% or greater of the $C_3$ hydrocarbons of the feed gas in said heavy hydrocarbon product or 95% or greater if recovered as the product of the optional distillation column.

Alternatively, the process of the present invention is operated such that a portion of the refrigeration necessary to perform the dephlegmation is supplied by reducing the temperature and pressure of the light gas stream by expanding the same through one or more expansion device(s), such as an expansion turbine.

Alternatively, the process of the present invention can include a distillation step whereby the heavy liquid is introduced as a feed stream into a distillation column. Said feed stream is separated into a second heavy liquid as a bottom product and a second light gas stream from the upper zone of said column.

Preferably in the distillative alternative, the process of the present invention is operated so that said heavy liquid stream from the phase separator is indirectly heat exchanged against the upper zone of the distillation column to provide reflux duty to said column.

Optionally in the distillative alternative, the process of the present invention is operated wherein said multicomponent refrigerant is indirectly heat exchanged against the upper zone of the distillation column to provide reflux duty to said column.

Preferably in the distillative alternative, the process of the present invention is operated wherein a slipstream or all of the feed gas or the multicomponent refrigerant is indirectly heat exchanged against the bottom zone of said distillation column to provide reboil duty to said column.

Preferably, the multicomponent refrigerant of the present process is composed predominantly of two or more components selected from the group comprising nitrogen, methane, ethane, propane, butane and pentane, as well as the unsaturated derivatives of such compounds.

Alternatively, the process of the present invention can be operated with a second stage of partial condensation and phase separation rather than a dephlegmator or refluxing heat exchanger. In that alternative, the process is operated in a similar manner except that the step of rectification by dephlegmation is deleted in favor of a process wherein the vapor stream is further cooled, phase separated into a light gas stream which is optionally expanded to a lower temperature and pressure and an additional heavy liquid stream wherein at least a portion of the cooling of the vapor stream is obtained by indirect heat exchange against a relatively low temperature and pressure stage of said multicomponent refrigerant.

DETAILED DESCRIPTION OF THE INVENTION

Figure 1:
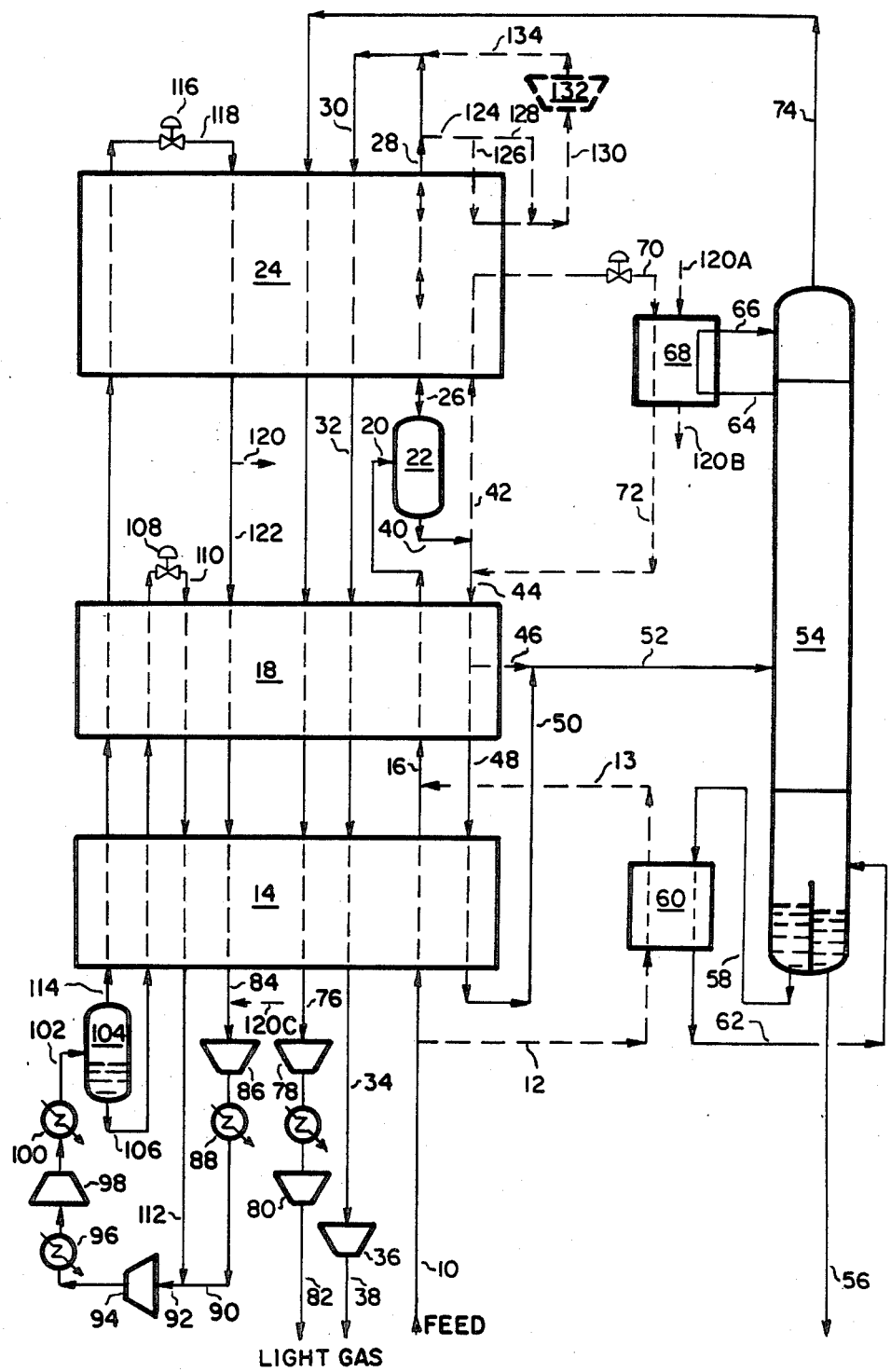
FIG. 1 is a schematic flowscheme of an embodiment of the process of the present invention showing various dotted line alternative configurations to the basic flowscheme.

The present invention provides an efficient process for the recovery of $C_{3+}$ hydrocarbons from a light gas stream. Such streams include natural gas streams containing NGL hydrocarbons, refinery off-gases, various petrochemical off-gas mixtures containing LPG hydrocarbons and dehydrogenation process off-gases containing $C_{3+}$ hydrocarbons. The present invention is particularly beneficial to the resolution of feed gases wherein high recovery levels of the $C_3$ components are desired, such recoveries being in the range of 90–99+% The feed gases can contain any number of light gas components and heavier hydrocarbons. Such light gas components include hydrogen, nitrogen, carbon monoxide and carbon dioxide as well as methane, ethane and ethylene. The heavier hydrocarbons can include propane, propylene, butane, butene, isobutane, isobutylene, and higher saturated and unsaturated hydrocarbons such as pentane, hexane and potentially residual amounts of even heavier hydrocarbons. Throughout the text of this patent, saturated and unsaturated hydrocarbons are symbolically referenced as the $C_{x+}$ designate of the carbon number of the hydrocarbon. The "+" symbol is utilized to indicate that the carbon atom count constitutes the designated number placed in the "x" subscript and higher molecular weight compounds.

The significant and unexpected improvement of the present invention in using low temperature phase separation, dephlegmation or a refluxing heat exchanger and, optionally, a distillation column, is derived from the particular type of refrigeration source utilized in the process of the present invention, wherein a multicomponent refrigerant is utilized in a two temperature and two pressure stage closed-circuit configuration. Effectively, the mixed or multicomponent refrigerant system is operated with two levels of evaporating refrigerant, a lighter relatively low pressure and low temperature mixture for colder levels of refrigeration in the refluxing heat exchanger or dephlegmator and a heavier relatively higher pressure and relatively higher temperature mixture for relatively warmer refrigeration in the first heat exchanger for the feed gas going to the phase separator and/or to condense the lighter refrigerant mixture. The overall composition of the mixed refrigerant and the pressure at which it is partially condensed to form the light vapor and heavier liquid fractions are selected to provide thermodynamically efficient temperature differences between the vaporizing mixed refrigerant streams and the condensing streams in both heat exchangers. The mixed or multicomponent refrigerant condensing temperature is generally determined by the available cooling medium, such as ambient air, cooling water or chilled water. This results in a highly energy efficient method to supply the refrigeration necessary to condense and recover the $C_3$ and heavier hydrocarbons in the feed stream as liquid product.

Alternatively, the mixed refrigerant may also supply condenser refrigeration in the upper zone of the optional integrated distillation column, either directly or indirectly, using either of the two evaporating pressure levels of the multicomponent refrigerant or by using the heavy liquid from the phase separation of the feed gas, or the heavy liquid from the dephlegmator.

The use of the multicomponent refrigerant cycle results in a significant power savings as compared to alternative methods of refrigeration supply. For example, using the preferred embodiment of FIG. 1, the $C_{3+}$ recovery from a natural gas feed stream using the mixed refrigerant process of the present invention requires 46% less power than the mixed refrigerant process described by MacKenzie, et al. recited in the prior art section of this application. At the same time, this process achieves 90% recovery of $C_3$ and 100% recovery of $C_{4+}$ components as compared to 79% $C_3$ recovery and 97% $C_{4+}$ recovery of the MacKenzie, et al. process.

There are significant differences between the two processes which account for the significantly improved performance of this process. In the MacKenzie, et al. process, the multicomponent refrigerant is compressed and partially condensed to form a light vapor and a heavier liquid refrigerant, with the light vapor subsequently being condensed. But both light and heavy liquids are revaporized at the same pressure for refrigeration supply. In the present invention, the light and heavy refrigerant mixtures are revaporized at two different pressure levels, which can be separately optimized to provide more efficient refrigeration supply (smaller temperature differences) in the separate heat exchangers.

Also in the MacKenzie, et al. process, both the light and heavy refrigerant mixtures are utilized for refrigeration supply over essentially the same temperature range, that is, ambient temperature to about $-100°$ F. In the process of the present invention, the light refrigerant supplies refrigeration predominately at the lower temperatures, and the heavier refrigerant supplies refrigeration at the warmer temperatures, which again results in a more efficient refrigeration supply.

Figure 2:
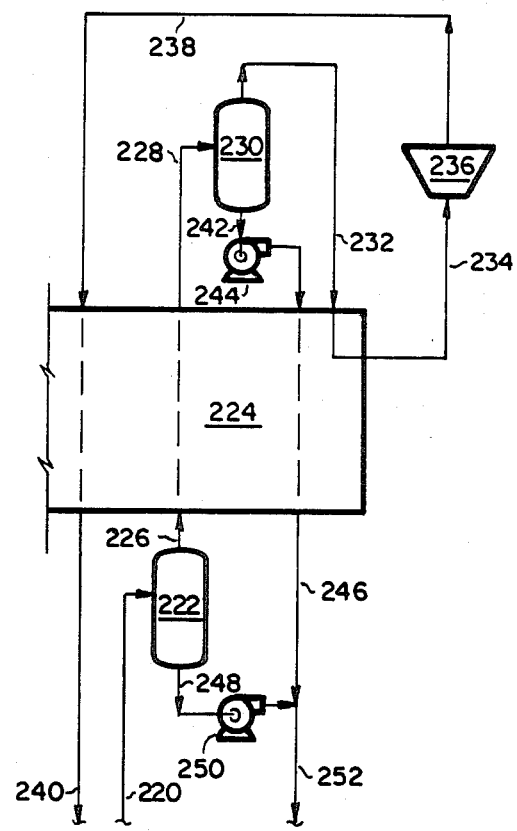
FIG. 2 is a partial flowscheme of an alternate embodiment of the present invention shown in part from the overall flowscheme of FIG. 1 wherein two stages of partial condensation and phase separation are used rather than rectification by dephlegmation.

When the process of the present invention as set forth in FIG. 1 is compared against the most energy efficient version of the Petroflux process of the UK patent application, FIGS. 2 and 3, and of the article by Tomlinson, et al., FIGS. 2 and 3, discussed in the prior art section of this application, it is seen that the present invention utilizes 35% less power. The Petroflux process as shown in the above noted Figures of the prior art utilizes a two-stage cascade refrigeration cycle for refrigeration. A "single loop . . . mixed refrigerant" cycle is mentioned as a possible alternative (see page 4, line 37 of the UK application), but is not otherwise described or shown, and it is furthermore stated that "the power saving will not be so great" as with the cascade system. A comparison of these two prior art cycles against the performance of the present invention is set forth in Tables 1 and 2 below.

TABLE 1
RELATIVE PERFORMANCE OF PRESENT INVENTION vs. PETROFLUX PROCESS*

|  |  | PRESENT INVENTION | PETROFLUX PROCESS* |
|---|---|---|---|
| FEED | LB MOLES/HR | 2750 | 2750 |
| $C_3$ RECOVERY | % | 92.1 | 92.1 |
| $C_{4+}$ RECOVERY | % | 100.0 | 100.0 |
| $C_{3+}$ PURITY | MOLE % | 86.0 | 86.0 |
| TOTAL POWER | HP | 470 | 720 |

*As disclosed in GB2146751A and Tomlinson, et al. article.

TABLE 2
RELATIVE PERFORMANCE OF PRESENT INVENTION vs. PROPAK PROCESS**

|  |  | PRESENT INVENTION | PROPAK PROCESS** |
|---|---|---|---|
| FEED | LB MOLES/HR | 1649 | 1649 |
| $C_3$ RECOVERY | % | 90.0 | 79.0 |
| $C_{4+}$ RECOVERY | % | 100.0 | 97.0 |
| $C_{3+}$ PURITY | MOLE % | 99.6 | 98.7 |
| TOTAL POWER | HP | 330 | 610 |

**As disclosed in MacKenzie, et al. article.

One embodiment of the process of the present invention will now be described in greater detail with reference to FIG 1. A feed gas is introduced in line 10 at 100° F. and 475 psia containing 65% methane, 24% nitrogen, 3.7% ethane, 2.5% propane, 1.9% helium, 0.9% butane, 0.4% isobutane, 0.4% hexane, 0.3% isopentane, 0.2% pentane and residual hydrocarbons and carbon dioxide. The feed gas in line 10 is cooled in a first heat exchanger 14 and then in line 16 is cooled in a second heat exchanger 18, which for purposes of the discussion will be considered a first overall heat exchanger. The feed gas is partially condensed as it exists in line 20 at a temperature of $-47°$ F. and a pressure of 469 psia. It is introduced into a phase separator vessel 22 to produce a heavy liquid stream containing heavy hydrocarbons in line 40 and a vapor stream containing light feed gas components in line 26. The stream in line 26 ascends a second overall heat exchanger 24 which consists of a refluxing heat exchanger or dephlegmator, wherein the vapor stream in line 26 is partially condensed, and the heavy condensed portion of the stream descends the heat exchange passageways to act as a reflux to rectify the vapor stream in line 26. The condensed portion of the stream returns under appropriate flow and temperature conditions to the phase separator vessel 22 to be combined with the stream initially phase separated as the heavy liquid stream in line 40. The light components which escape overhead from the dephlegmator 24 are removed in line 28 at a temperature of $-127°$ F. and a pressure of 469 psia. This stream is returned in line 30 through the heat exchanger 24, and after being rewarmed in that heat exchanger, the stream, now in line 32, passes through exchanger 18 and 14 and is removed in line 34 at a temperature of 94° F. and a pressure of 462 psia. It can be recompressed to pipeline pressure in a compressor 36 before being removed in line 38 as product light gas containing 2.0% helium, 26.2% nitrogen, 68.5% methane and 3.0% ethane, along with residual propane and carbon dioxide.

The heavy liquid stream is passed through line 44 into heat exchanger 18 and then in line 48 through heat exchanger 14 for rewarming before being introduced through line 50 and 52 as a feed to the distillation column 54 for further purification. The distillation column 54 is operated with a condenser in its upper zone and a reboiler in its bottom zone. A heavy hydrocarbon product containin $C_{3+}$ hydrocarbons is derived from the bottom zone of the column 54 in line 56. A portion of the liquid phase settling into the bottom zone of the distillation column 54 is removed in line 58, vaporized in the heat exchanger 60 and returned in line 62 to the distillation column as reboil for the column. This circuit constitutes the reboiler. A second light gas stream is removed from the upper zone of the column 54 in line 74. This stream is rewarmed through the heat exchangers 24, 18 and 14 before leaving the process in line 76 at a temperature of 94° F. and 56 psia, after which the stream can be compressed in a compressor 78, aftercooled and further compressed in the compressor 80 and removed as a stream in line 82 constituting a product light gas stream having similar compositional characteristics as the product light gas stream in line 38.

The distillation column 54 operates at a pressure of approximately 60 psia and in addition to the reboil function previously described, a condenser duty is provided in the upper zone of the column by removal of a vapor stream in line 64 to be cooled and partially condensed in heat exchanger 68 and returned as reflux in line 66. This circuit constitutes the condenser.

A predominant amount of the refrigeration necessary to operate the process described and illustrated in FIG. 1 is derived from a multicomponent refrigerant cycle, which is operated in a closed-circuit configuration. The refrigerant can be derived from any number of components, but is preferably selected from the group comprising nitrogen, methane, ethane, propane, butane and pentane, as well as unsaturated derivatives of these compounds. In the present embodiment, the refrigerant is comprised of predominantly ethane with a lesser amount of butane, as well as methane and a small amount of propane. With reference to FIG. 1, the refrigerant in line 92 is at a temperature of 98° F. and a pressure of 43 psia. It is recompressed in compressor 94 and aftercooled in aftercooling heat exchanger 96 before being further compressed in compressor 98 and again aftercooled in aftercooling heat exchanger 100, usually against cooling water, before being introduced in line 102 into a phase separator 104. In line 102, the refrigerant is at approximately 100° F. and a pressure of 350 psia. In the phase separation vessel 104, the refrigerant is separated into a light vapor phase derived in line 114 and a heavy liquid phase derived in line 106.

The liquid phase in line 106 is cooled against itself and process streams in heat exchanger 14 and 18 before being reduced in temperature and pressure through valve 108 and reintroduced into the heat exchangers in line 110. The refrigerant in line 110 is expanded to a relatively high temperature and pressure of −55° F. and 49 psia. It then provides refrigeration duty by rewarming in indirect heat exchange with process streams, and particularly the feed gas, in heat exchangers 18 and 14 before being returned in line 112 to be combined with the stream in line 90.

The light vapor phase multicomponent refrigerant from phase separation vessel 104 is removed in line 114, cooled and condensed against itself and process streams in heat exchangers 14, 18 and 24 before being reduced in temperature and pressure in valve 116 to a temperature of −159° F. and a pressure of 21 psia, which is deemed to be the relatively low temperature and pressure. This stream in line 118 then provides cooling for the dephlegmation in heat exchanger 24 and in part for the cooling of the feed gas in heat exchangers 18 and 14, wherein the refrigerant passes as stream 122 through these latter two heat exchangers and is returned in line 84 at a temperature of 96° F. and a pressure of 15 psia before being recompressed in compressor 86, aftercooled in aftercooling heat exchanger 88 and returned in line 90.

As shown in dotted line configuration, a slipstream 12 of the feed gas 10 can optionally be removed and passed through heat exchanger 60 to provide heat for the reboil function of the distillation column 54 before the slipstream in line 13 is returned to the feed gas which is cooling in line 16. Alternatively, the reboil function can be operated by passing a slipsteam of the refrigerant from compressor 98 through the heat exchanger 60 and returning it to line 102 (not illustrated).

In addition, another alternative provides for the utilization of refrigeration value from the heavy liquid stream 40 separated from the feed gas in the phase separation vessel 22, wherein a portion or all of the heavy liquid stream is removed in line 42 and may be further cooled in heat exchanger or dephlegmator 24 before being reduced in pressure in line 70 and rewarmed in condensing heat exchanger 68, which provides condensing duty for the upper zone of the distillation column 54. The heavy liquid stream, after being rewarmed, may be returned in line 72 to the main stream flow in line 44. In this event, it may be preferable, although not required, that the stream is taken only partially through heat exchanger 18 and removed in line 46 for introduction into the distillation column 54 through line 52.

A further alternative allows the light gas stream in line 28 to be used as a source of additional refrigeration wherein all or a portion of the stream is diverted in line 124 and split into streams 126 and 128 wherein a portion or all of the stream may, if desired, be passed through heat exchanger 24 before the combined streams in line 130 are expanded in one or more expansion turbine(s) 132 to a lower temperature and pressure and returned in line 134 and line 30 to provide refrigeration duty in the refluxing heat exchanger or dephlegmator 24.

A final alternative allows a slipstream of multicomponent refrigerant in line 120 to be removed and introduced into the condensing heat exchanger 68 through line 120A and recovered in line 120B after providing refrigeration. The mixed component refrigerant in line 120B is then returned, for example, in line 120C to main line 84 of the multicomponent refrigerant low pressure stage.

The heavy liquid may be fractionated in a distillation column, as described above, to remove residual methane, and/or $C_2$ hydrocarbons or other light gases in order to produce a $C_{3+}$ hydrocarbon product of higher purity, but the distillation step is not necessary in some embodiments of the invention, where higher purity is not necessary.

It is possible to insert a baffle in the phase separator 22 such that the initial (first) heavy liquid separated in the phase separator is segregated from the additional (second) heavy liquid derived from dephlegmation of the vapor stream of line 26 passing through heat exchanger 24. These two heavy liquid streams are recovered as product or for feed to a distillation column.

It may be preferable, but not required, to recover the first and second heavy liquid streams separately, rather than as a combined stream. For example, it may be desirable to introduce the first and second liquid streams separately into a distillation column, to achieve more efficient operation of the column, or to warm the two liquid streams separately, for more efficient refrigeration recovery.

Although the preferred embodiment of the present invention uses a refluxing heat exchanger, it is possible to use a second stage of partial condensation and phase separation as set forth in FIG. 2. In FIG. 2 the drawing shows an isolation of the light vapor stream treatment portion of the overall process only. All the rest of the process is essentially arranged and operated in the manner of FIG. 1. Accordingly, the feed gas stream in line 220 of FIG. 2 (similar to line 20 of FIG. 1) is introduced into a phase separation vessel 222, wherein a vapor stream in line 226 is removed and cooled without refluxing in a heat exchanger 224, before the cooled vapor stream in line 228 is introduced into a second phase separation vessel 230. In this second vessel 230, a final light gas stream is removed in line 232, optionally rewarmed in the heat exchanger 224 and introduced in line 234 into expansion turbine 236 for reduction in temperature and pressure, before returning in line 238 to the heat exchanger 224 to provide additional refrigeration. The stream is removed in line 240 and is processed similarly to stream 32 of FIG. 1. The heavy liquid stream 242 from the second phase separation vessel 230 may be pumped to higher pressure in pump 244 before being rewarmed in the heat exchanger 224 and combined in line 246 with the heavy liquid stream 248 from the first phase separation vessel 222 after it also has been pumped to elevated pressure in pump 250 and combined to make a combined heavy liquid stream in line 252, which is treated similarly to stream 40 of FIG. 1. The heavy liquid streams may optionally be recovered separately. All of the other portions of the overall process are the same as in FIG. 1, but this FIG. 2 configuration exchanges a series partial condensation and phase separation process scheme for the single partial condensation, phase separation and dephlegmation embodiment of FIG. 1.

The various preferred embodiments of the present invention have been set forth in detail, wherein the particular configuration of the present invention provides an unexpected and significant benefit over various prior art cycles as set forth in Tables 1 and 2 above. The dramatic effect of the results of comparative analysis of the present invention over such cycles exemplified in the Tables demonstrates the unique novelty of the present invention and shows a decided improvement and efficiency in the processing of such light gas streams.

The present invention should not be limited to the particular embodiments disclosed, but rather should be construed in light of the claims which follow.

We claim:

1. A process for the low temperature separation of a feed gas into a heavy hydrocarbon product containing $C_{3+}$ hydrocarbons and a light gas stream containing $H_2$, $N_2$, CO, $CO_2$, methane and/or $C_2$ hydrocarbons or other light gases using a two temperature and two pressure stage, closed-circuit, multicomponent refrigerant cycle comprising the steps of:
   (a) cooling the feed gas to effect the partial condensation of said gas by indirect heat exchange against a relatively high temperature and pressure stage of said multicomponent refrigerant;
   (b) initially phase separating the partially condensed feed gas into a heavy liquid containing heavy hydrocarbons and a vapor stream containing light feed gas components;
   (c) rectifying the vapor stream by low temperature dephlegmation to produce a light gas stream and additional heavy liquid wherein the rectification is obtained at least in part by indirect heat exchange against a relatively low temperature and pressure stage of said multicomponent refrigerant;
   (d) removing said heavy liquid as a heavy hydrocarbon product containing $C_{3+}$ hydrocarbons;
   (e) removing the light gas stream of step (c) as a product light gas stream containing $H_2$, $N_2$, CO, $CO_2$, methane and/or $C_2$ hydrocarbons or other light gases; and
   (f) providing the predominant amount of the refrigeration for the process from said closed-circuit, multicomponent, refrigerant cycle wherein the refrigerant is partially condensed phase separated, the vapor phase is cooled, condensed and expanded to a relatively low temperature and pressure and rewarmed against the vapor stream being rectified and then recompressed to an intermediate pressure, while the liquid phase is cooled, expanded to a relatively higher temperature and pressure, rewarmed against feed gas, mixed with the intermediate pressure refrigerant and the combined refrigerant is compressed to an elevated pressure and aftercooled sufficiently to partially condense the refrigerant to complete the circuit.

2. The process of claim 1 wherein 90% of the $C_3$ hydrocarbons of the feed gas are recovered in said heavy hydrocarbon product.

3. The process of claim 1 wherein 98% of the $C_3$ hydrocarbons of the feed gas are recovered in said heavy hydrocarbon product.

4. The process of claim 1 wherein a portion of the refrigeration necessary to perform the dephlegmation is supplied by reducing the temperature and pressure of the light gas stream by expanding the same through one or more expansion device(s).

5. The process of claim 1 wherein the multicomponent refrigerant is composed predominantly of two or more components selected from the group of: nitrogen, methane, ethane, propane, butane and pentane and unsaturated derivatives of those compounds.

6. The process of claim 1 wherein said product light gas stream is predominantly methane.

7. A process for the low temperature separation of a feed gas into a heavy hydrocarbon product containing $C_{3+}$ hydrocarbons and a light gas stream containing $H_2$, $N_2$, CO, $CO_2$, methane and/or $C_2$ hydrocarbons or other light gases using a two temperature and two pressure stage closed-circuit multicomponent refrigerant cycle comprising the steps of:
   (a) cooling the feed gas to effect the partial condensation of said gas by indirect heat exchange against a relatively high temperature and pressure stage of said multicomponent refrigerant;
   (b) initially phase separating the partially condensed feed gas into a heavy liquid containing heavy hydrocarbons and a vapor stream containing light feed gas components;
   (c) further cooling the vapor stream, phase separating the stream into a light gas stream and additional heavy liquid wherein at least a portion of the cooling is obtained by indirect heat exchange against a relatively low temperature and pressure stage of said multicomponent refrigerant;

(d) recovering said heavy liquid as a heavy hydrocarbon product containing $C_{3+}$ hydrocarbons;

(e) removing the light gas stream of step (c) as product light gas stream containing $H_2$, $N_2$, $CO$, $CO_2$, methane and/or $C_2$ hydrocarbons or other light gases; and (f) providing the predominant amount of the refrigeration for the process from said closed-circuit multicomponent refrigerant cycle wherein the refrigerant is partially condensed, phase separated, the vapor phase is cooled, condensed and expanded to a relatively low temperature and pressure and rewarmed against the vapor stream being cooled and then recompressed to an intermediate pressure, while the liquid phase is cooled, expanded to a relatively higher temperature and pressure, rewarmed against feed gas, mixed with the intermediate pressure refrigerant and the combined refrigerant is compressed to an elevated pressure and aftercooled sufficiently to partially condense the refrigerant to complete the circuit.

8. A process for the low temperature separation of a feed gas into a heavy hydrocarbon product containing $C_{3+}$ hydrocarbons and a light gas stream containing $H_2$, $N_2$, $CO$, $CO_2$, methane and/or $C_2$ hydrocarbons or other light gases using a two temperature and two pressure stage, closed-circuit, multicomponent refrigerant cycle comprising the steps of:

(a) cooling the feed gas to effect the partial condensation of said gas by indirect heat exchange against a relatively high temperature and pressure stage of said multicomponent refrigerant;

(b) initially phase separating the partially condensed feed gas into a heavy liquid containing heavy hydrocarbons and a vapor stream containing light feed gas components;

(c) rectifying the vapor stream by low temperature dephlegmation to produce a first light gas stream and additional heavy liquid wherein the rectification is obtained at least in part by indirect heat exchange against a relatively low temperature and pressure stage of said multicomponent refrigerant;

(d) introducing said heavy liquid into a distillation column as feed to said column;

(e) separating said liquid of step (d) in said distillation column into a heavy hydrocarbon product containing $C_{3+}$ hydrocarbons derived from the bottom zone of said column and a second light gas stream derived from the upper zone of said column;

(f) removing the first light gas stream of step (c) and the second light gas stream of step (e) as product light gas streams containing $H_2$, $N_2$, $CO$, $CO_2$, methane and/or $C_2$ hydrocarbons or other light gases; and (g) providing the predominant amount of the refrigeration for the process from said closed-circuit, multicomponent, refrigerant cycle wherein the refrigerant is partially condensed, phase separated, the vapor phase is cooled, condensed and expanded to a relatively low temperature and pressure and rewarmed against the first vapor stream being rectified and then recompressed to an intermediate pressure, while the liquid phase is cooled, expanded to a relatively higher temperature and pressure, rewarmed against feed gas, mixed with the intermediate pressure refrigerant and the combined refrigerant is compressed to an elevated pressure and aftercooled sufficiently to partially condense the refrigerant to complete the circuit.

9. The process of claim 8 wherein 95% of the $C_3$ hydrocarbons of the feed gas are recovered in said heavy hydrocarbon product.

10. The process of claim 8 wherein said heavy liquid stream of step (c) is indirectly heat exchanged against the upper zone of said distillation column to provide reflux duty to said column.

11. The process of claim 8 wherein said multicomponent refrigerant is indirectly heat exchanged against the upper zone of said distillation column to provide reflux duty to said column.

12. The process of claim 8 wherein a slipstream or all of the feed gas is indirectly heat exchanged against the bottom zone of said distillation column to provide reboil duty to said column.

13. The process of claim 8 wherein said multicomponent refrigerant is indirectly heat exchanged against the bottom zone of said distillation column to provide reboil duty to said column.

14. The process of claim 8 wherein said first light gas stream and said second light gas stream are combined as a product light gas stream.

15. A process for the low temperature separation of a feed gas into a heavy hydrocarbon stream containing $C_{3+}$ hydrocarbons and a light gas stream containing $H_2$, $N_2$, $CO$, $CO_2$, methane and/or $C_2$ hydrocarbons or other light gases using a two temperature and two pressure stage closed-circuit multicomponent refrigerant cycle comprising the steps of:

(a) cooling the feed gas to effect the partial condensation of said gas by indirect heat exchange against a relatively high temperature and pressure stage of said multicomponent refrigerant;

(b) initially phase separating the partially condensed feed gas into a heavy liquid stream containing heavy hydrocarbons and a vapor stream containing light feed gas components;

(c) further cooling the vapor stream, phase separating the stream into a first light gas stream and additional heavy liquid, wherein at least a portion of the cooling is obtained by indirect heat exchange against a relatively low temperature and pressure stage of said multicomponent refrigerant;

(d) introducing said heavy liquid into a distillation column as feed to said column;

(e) separating said liquid in said distillation column into a heavy hydrocarbon product containing $C_{3+}$ hydrocarbons derived from the bottom zone of said column and a second light gas stream derived from the upper zone of said column;

(f) removing the first light gas stream of step (c) and the second light gas stream of step (e) as product light gas streams containing $H_2$, $N_2$, $CO$, $CO_2$, methane and/or $C_2$ hydrocarbons or other light gases; and (g) providing the predominant amount of the refrigeration for the process from said closed-circuit multicomponent refrigerant cycle wherein the refrigerant is partially condensed, phase separated, the vapor phase is cooled, condensed and expanded to a relatively low temperature and pressure and rewarmed against the first vapor stream being cooled and then recompressed to an intermediate pressure, while the liquid phase is cooled, expanded to a relatively higher temperature and pressure, rewarmed against feed gas, mixed with the intermediate pressure refrigerant and the combined refrigerant is compressed to an elevated pressure and aftercooled sufficiently to partially condense the refrigerant to complete the circuit.

* * * * *